United States Patent [19]

Castro et al.

[11] Patent Number: 5,176,902
[45] Date of Patent: * Jan. 5, 1993

[54] COLORED COSMETIC STICKS OF IMPROVED HARDNESS

[75] Inventors: John R. Castro, Stamford; John D. Strickland, Beacon Falls, both of Conn.; John A. Szweda, River Vale, N.J.; Richard T. Rigg, Springfield Garden, N.Y.

[73] Assignee: Elizabeth Arden Company, Division of Conopco, Inc., New York, N.Y.

[*] Notice: The portion of the term of this patent subsequent to Apr. 28, 2009 has been disclaimed.

[21] Appl. No.: 802,687

[22] Filed: Dec. 5, 1991

[51] Int. Cl.$^5$ ................... A61K 7/021; A61K 7/028
[52] U.S. Cl. ................................ 424/63; 424/64; 106/404
[58] Field of Search ............... 424/401, 63, 64, 68

[56] References Cited

U.S. PATENT DOCUMENTS 4,172,123 10/1979 Lowicki ........................ 424/76.4
4,722,836 11/1988 Geary ............................. 424/67

FOREIGN PATENT DOCUMENTS 61-83110 4/1986 Japan .

Primary Examiner—Thurman K. Page
Assistant Examiner—Sally Gardner
Attorney, Agent, or Firm—Milton L. Honig

[57] ABSTRACT

A method is provided for producing a colored cosmetic stick or reproducible hardness through utilizing a wax that has been treated with an alcohol to convert any naturally-occurring $C_{12}$–$C_{60}$ fatty acid into a respective ester. This esterified wax is mixed with an aluminum lake colorant and then formed into a stick. There is also disclosed colored cosmetic sticks produced through the aforementioned process.

8 Claims, No Drawings

COLORED COSMETIC STICKS OF IMPROVED HARDNESS

BACKGROUND OF THE INVENTION

1. Field of the Invention

The invention relates to a colored cosmetic stick of improved rigidity for use especially as a lipstick.

2. The Related Art

Traditional lipsticks are formulated with hydrophobic ingredients such as triglyceride or fatty acid ester derived oils and waxes. In particular, the waxes are important to impart the requisite stiffness or rigidity for structurant purposes.

A problem occasionally arises when a batch of lipstick inexplicitly turns too soft thereby drawing the composition outside the hardness specification. Not only are these odd batches a quality control problem, but there is a direct negative impact upon production costs when an errant batch must be discarded. Causes of the problem have not been fully identified.

Accordingly it is an object of the present invention to provide a colored cosmetic stick, especially a lipstick, formulated with hydrophobic ingredients including oils and waxes which result in a product of reproducibly satisfactory hardness.

Another object of the present invention is to provide a colored cosmetic stick, especially a lipstick, that can be rendered reproducibly hard in a cost efficient method.

A still further object of the present invention is to provide a colored cosmetic stick, especially a lipstick, formulated with both yellow and red colorants that will have good color impact while maintaining structural and aesthetic integrity.

These and other objects, features and advantages of the present invention will become more readily apparent through consideration of the following summary, detailed description and examples which follow.

SUMMARY OF THE INVENTION

Now it has been found that traces of water, sometimes considerably less than 0.3% water, may adversely interact with colorants such as aluminum salts or lakes which then further react with $C_{12}$–$C_{60}$ fatty acids to form aluminum soaps. These soaps act as crystal poisons which cause the stick to lose structure. Thus, compositions of the present invention should be formulated with less than an effective amount of the $C_{12}$–$C_{60}$ fatty acid that would otherwise form a soap with aluminum lakes. While fatty acids are not often purposely formulated with colored cosmetic sticks, these materials are often present as substantial impurities in standard waxes such as candelilla, ozokerite, carnauba, beeswax, lanolin and spermaceti waxes.

Armed with this insight, a method has been devised for manufacturing colored cosmetic sticks that insures reproducible hardness. The method comprises:

(i) selecting a wax that has been esterified with an alcohol to convert all naturally present $C_{12}$–$C_{60}$ fatty acid into a respective ester;

(ii) mixing the esterified wax in an amount from about 1 to about 99% with a colorant which is an aluminum salt in an amount from about 0.001 to about 20%; and (iii) forming a colored cosmetic stick with the mixture from step (ii).

In another aspect of the invention there is provided a colored cosmetic stick comprising:

(i) from about 1 to about 99% of a natural wax;

(ii) from about 0.001 to about 20% of a colorant which is an aluminum salt; and (iii) from about 0.001 to about 20% of a $C_{12}$–$C_{60}$ fatty acid ester; and wherein is absent any $C_{12}$–$C_{60}$ fatty acid.

DETAILED DESCRIPTION

The manufacture of a reproducibly rigid colored cosmetic stick requires provision of a wax which is free from any $C_{12}$–$C_{60}$ fatty acid, especially fatty monocarboxylic acid, an impurity normally present in the natural waxes. This impurity may be counteracted through esterification with a molar equivalent or more of a $C_1$–$C_{60}$ mono or polyhydric alcohol. Particularly preferred are the $C_1$–$C_{60}$ monohydric alcohols. Illustrative alcohols useful herein include methanol, ethanol, lauryl alcohol, palmitic alcohol and combinations thereof.

The esterification process involves combining the natural wax with from 0.5 to 20% of the alcohol in a vessel under agitation at a temperature of anywhere from about 40° C. to about 250° C., preferably from about 80° C. to about 150° C.

Advantageously, a vacuum is applied to the vessel to remove water vapor formed in the esterification. An effective amount of a Lewis acid catalyst may be employed, for instance, a mineral acid (e.g. sulfuric or hydrochloric acid), an organic acid (e.g. toluene sulfonic acid) or an inorganic substance such as boron trifluoride etherate.

The natural waxes suitable for the present invention are normally low-melting organic compounds of high molecular weight, solid at room temperature and generally similar in composition to fats and oils, except that they contain no glycerides. Waxes are thermoplastic, but since they are not high polymers, they are not considered in the family of plastics. Among the natural waxes are those of animal origin (beeswax, spermaceti, lanolin, shellac wax) and vegetable origin (carnauba, candelilla, bayberry, sugarcane wax). Most preferred are candelilla, carnauba, beeswax, lanolin and spermaceti waxes.

Amounts of the wax may range anywhere from about 1 to about 99% by weight, preferably from about 10 to about 50%, optimally between about 15 and about 25% by weight.

Compositions of the present invention will contain from about 0.001 to about 20% by weight of a colorant which is an aluminum salt. Amounts of colorant will preferably range from about 0.1 to about 10%, optimally from about 0.5 to about 8% by weight.

Advantageously, the aluminum salt is an aluminum lake. Lakes are either a pigment that is extended or reduced with a solid diluent or an organic pigment that is prepared by the precipitation of a water-soluble dye on an adsorptive surface, which usually is alumina hydrate. There is uncertainty in some instances as to whether the soluble dye precipitates on the surface of the alumina hydrate to yield a dyed inorganic pigment or whether it merely precipitates in the presence of the substate. A lake also forms from precipitation of an insoluble salt from an acid or basic dye.

Particularly preferred aluminum lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake.

Beyond the basic components of the present invention, there optionally may be other ingredients which serve to enhance product function and aesthetics. These optional ingredients are detailed below.

Emulsifiers may be incorporated in the cosmetic formulations of the present invention. Overall concentration of emulsifier may range anywhere from about 0.1 to about 30% by weight of the formulation, preferably from about 0.5 to about 20%, optimally between about 2 and 10% by weight.

Phospholipids is an important category of emulsifiers that may contribute to the stability and pleasing appearance of the composition.

Examples of phospholipids are those within the categories of phosphoglycerides, lysophosphoglycerides, sphingomyelins and mixtures thereof. Especially useful as a phospholipid is lecithin.

Fatty acid derivative-type emulsifiers may also be employed, especially in combination with a phospholipid. These emulsifiers may include monoacyl glycerol, diacyl glycerol and polyglycerol esters and combinations thereof. Especially preferred are glycerol monoalkanoates, an example of which are the monoglycerides of sunflower seed oil and of palm oil.

Emollient oils which are defined as oily organic substances liquid at room temperature (i.e. 20° C.) can be employed singly or as mixtures of two or more oils. They normally will be present at levels from about 2 to about 97%, preferably from about 30 to 70% by weight of the composition.

These oils are useful not only for emollient purposes but may also impart viscosity, tackiness and drag properties. Examples of suitable oils include caprylic triglycerides; capric triglycerides; isostearic triglycerides; adipic triglycerides; propylene glycol myristyl acetate; lanolin oil; polybutene; isopropyl palmitate; isopropyl myristate; diethyl sebacate; diisopropyl adipate; hexadecyl stearate; cetyl oleate; oleyl alcohol; hexadecyl alcohol; wheatgerm oil; hydrogenated vegetable oils; petrolatum; modified lanolins; branched-chain hydrocarbons, alcohols and esters; castor oil; corn oil; cottonseed oil; olive oil; palm kernel oil; rapeseed oil; safflower seed oil; jojoba oil; evening primrose oil; avocado oil; mineral oil; and volatile and non-volatile silicone oils.

Skin active ingredients in the form of both water-soluble and insoluble substances may be included within the formulations of this invention. These ingredients may range anywhere from about 0.0001 to about 10% by weight. Examples include zinc oxide; β-glycyrrhetic acid; chamomile oil; ginko biloba extract; pyroglutamic acid, salts or esters; sodium hyaluronate; 2-hydroxyoctanoic acid; sulphur; salicylic acid; carboxymethyl cysteine and mixtures thereof.

The following examples will more fully illustrate certain aspects of the present invention. All parts, percentages and proportions referred to herein and in the appended claims are by weight unless otherwise indicated.

EXAMPLE

Beeswax containing free fatty acids was heated along with a $C_{14}$–$C_{16}$ alcohol mixture to 200° C. under a vacuum of approximately 7 inches for approximately three hours. Lipsticks were prepared having the following formula:

| Ingredient | % Weight |
| --- | --- |
| Castor oil | 19.5 |
| Isopropyl palmitate | 11.6 |
| Caprylic/capric/isostearic/adipic triglyceride | 7.0 |
| Lanolin | 7.0 |
| Red 21 Aluminum Lake | 7.0 |
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |
| Carnauba wax | 0.4 |

Lipsticks similar in composition to those above were formulated with the waxes still retaining their free fatty acid impurities ("Non Esterified"). Other sticks were formed from the same waxes that were, however, esterified. Table I describes the results of various physical property tests on both sets of lipsticks.

TABLE I

Rheological and Stability Results

| | Crush (g) | Break (g) | Phase *Stability |
| --- | --- | --- | --- |
| Esterified Waxes | 3,200.0 | 425.0 | No oil exudation |
| Non Esterified | 600 | 200 | Oil exudation |

Phase stability was measured by a freeze/thaw test. Samples of the lipstick were subjected to freeze/thaw cycling between 0° C./45° C., 40° C. and room temperature. Crush and break measurements were obtained on a Chatillion apparatus.

An acceptable lipstick normally will have crush and break values of greater than 2,000 g and 400 g, respectively. Only the esterified wax formula provided acceptable crush, break and stability values. There was also a quite noticeable increase in surface gloss in the formulas containing esterified waxes which is an indication of relatively good crystalline structure.

The foregoing description and example illustrate selected embodiments of the present invention. In light thereof, various modifications will be suggested to one skilled in the art, all of which are within the spirit and purview of this invention.

What is claimed is:

1. A method for preparing a colored cosmetic stick which is a lipstick comprising:
   (i) selecting a wax that has been esterified with a $C_1$–$C_{60}$ mono or polyhydric alcohol to convert all naturally present $C_{12}$–$C_{60}$ fatty acid into a respective ester;
   (ii) mixing the esterified wax in an amount from about 1 to about 99% with a colorant which is an aluminum lake in an amount from about 0.001 to about 20%; and
   (iii) forming a colored cosmetic stick with the mixture from step (ii).

2. The method of claim 1 wherein said aluminum lake is selected from the group consisting of Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake, Blue 1 Aluminum Lake and combinations thereof.

3. The method according to claim 1 wherein said alcohol is a $C_1$–$C_{60}$ alcohol.

4. The method according to claim 1 wherein the wax is selected form the group consisting of candelilla, carnauba, beeswax, lanolin, spermaceti and wax mixtures thereof.

5. A colored cosmetic stick which is a lipstick comprising:
  (i) from about 1 to about 99% of a natural wax;
  (ii) from about 0.001 to about 20% of a colorant which is an aluminum lake; and
  (iii) from about 0.001 to about 20% of a $C_{12}$–$C_{60}$ fatty acid ester; and
  wherein is absent any $C_{12}$–$C_{60}$ fatty acid.

6. The colored cosmetic stick according to claim 5 wherein the aluminum lake is selected from the group consisting of Red 3 Aluminum Lake, Red 21 Aluminum Lake, Red 27 Aluminum lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake, Blue 1 Aluminum Lake and combinations thereof.

7. The colored cosmetic stick according to claim 5 wherein the wax is selected form the group consisting of candelilla, carnauba, beeswax, lanolin, spermaceti and wax mixtures thereof.

8. The colored cosmetic stick according to claim 5 wherein said wax is present in an amount of from about 10 to about 50% by weight.

* * * * *